United States Patent [19]

Kramer et al.

[11] 4,171,909
[45] Oct. 23, 1979

[54] APPARATUS FOR MEASURING LIGHT INTENSITIES

[75] Inventors: Donald L. Kramer; James A. White, both of Elkhart, Ind.

[73] Assignee: Miles Laboratories, Inc., Elkhart, Ind.

[21] Appl. No.: 781,180

[22] Filed: Mar. 25, 1977

[51] Int. Cl.² .......................................... G01N 21/22
[52] U.S. Cl. ................................. 356/73; 356/435; 356/436; 356/448
[58] Field of Search ............... 356/180, 186, 201, 206, 356/207, 209, 210, 212, 202, 204, 208, 72, 73, 409, 414, 432, 433, 435, 436, 445, 446, 438

[56] References Cited

U.S. PATENT DOCUMENTS

| | | | |
|---|---|---|---|
| 2,601,182 | 6/1952 | Tyler | 356/210 |
| 3,327,583 | 6/1967 | Vanderschmidt et al. | 356/210 |
| 3,490,849 | 1/1970 | Hambleton | 356/206 |
| 3,746,869 | 7/1973 | Lindstedt et al. | 356/73 |
| 3,792,268 | 2/1974 | Bjerke et al. | 356/210 |
| 3,810,696 | 5/1974 | Hutchins | 356/97 |

FOREIGN PATENT DOCUMENTS

| | | | |
|---|---|---|---|
| 897728 | 3/1945 | France | 356/201 |
| 158107 | 3/1964 | U.S.S.R. | 356/186 |

Primary Examiner—John K. Corbin
Assistant Examiner—R. A. Rosenberger
Attorney, Agent, or Firm—Roger N. Coe

[57] ABSTRACT

Apparatus for measuring reflected or transmitted light is described. The apparatus comprises filter type spectrophotometer having a wavelength range of from about 200 nm (nanometers) to about 1,100 nm which includes a sample illuminating light source capable of producing an extremely intense light of short duration; light diffusing means; a light filter for transmission of a selected wave-length; at least two independent light sensing means; and separate means defining light transmission paths for the passage of light from the light source to one light sensing means and from the illuminated sample to the other light sensing means.

In a preferred embodiment the apparatus includes a light diffusing integrating sphere. In another embodiment, a replaceable or repositionable module can be used to convert the apparatus from reflectance to transmittance spectrophotomer.

10 Claims, 5 Drawing Figures

APPARATUS FOR MEASURING LIGHT INTENSITIES

FIELD OF THE INVENTION

The present invention relates to an instrument capable of making reflectance or transmittance measurements and more particularly, the present invention is directed to an improved filter type spectrophotometer capable of making either reflectance or transmittance measurements.

BACKGROUND OF THE INVENTION

Reflectance meters employing photoelectric cells to determine color values by measuring the amount of light reflected from a colored surface illuminated by a reference light source are well-known. These prior art reflectance meters have several disadvantages when it is sought to use them to quickly measure color values of analytical test devices, such as bibulous carriers impregnated with chemical reagent systems.

For some instruments, one of the disadvantages is the time and care required for making standardization adjustments. Repeated adjustments are required to compensate existing equipment for time and temperature variations. In particular, variations can occur using such equipment due to varying power to the light source. Power adjustments of prior art instruments generally corrected only the voltage and/or current to provide a substantially constant power input to the light source. Despite such adjustments error in the calibration of instruments could occur as a function of short term changes in light output from the light source or short term changes in sensitivity of the photoelectric cells. Repeated recalibration is not only an inconvenience, but it can introduce measurement errors if the recalibration is not accurately performed. Skilled personnel are accordingly required to operate the instruments.

Another major disadvantage of prior art instruments is the amount of heat generated by the light source and, concomitantly, the amount of power required for the light source. The utilization of heat filters to protect samples does not obviate this problem. Such heat filters do not minimize power requirements and they do reduce the intensity of the light source which can be effectively utilized. Substitution of shutter arrangements for heat filters to permit the utilization of full light intensity has also been suggested, but does not minimize the power requirements.

Prior art instruments also had a common drawback of being generally large in size and of substantial weight. Such instruments tended to be expensive due to their size, complexity and the necessity of adapting the equipment for regulation of heat generated during use. Some instruments were not even readily convertible for making both reflectance and transmittance measurements.

Still another problem with many existing reflectance meters is the fact that care must be exercised to regulate ambient light conditions during use in order not to affect the accuracy of the meters.

SUMMARY OF THE INVENTION

An object of the present invention is to provide an improved filter type spectrophotometer.

Another object of the present invention is to provide a relatively inexpensive instrument for making either reflectance or transmittance measurements.

Still another object of the present invention is to provide a filter type spectrophotometer having a cool light source of uniform light intensity.

Yet another object of the present invention is to provide a spectrophotometer which can be used without requiring calibration by highly skilled operators.

A further object of the present invention is to provide a relatively compact readily portable instrument for measuring light intensities.

In accordance with the present invention, an instrument is provided for measuring light reflected from a colored surface or transmitted through a colored substance. The instrument comprises an extremely intense, short duration sample illuminating light source; a light filter; light sensing means; and means defining separate light transmission paths for the passage of light from the light source to one light sensing means and from an illuminated sample to the other light sensing means. In a preferred embodiment the instrument includes an integrating sphere.

In the reflectance mode the instrument is especially useful for measuring color values of analytical test devices, such as bibulous carriers impregnated with chemical reagent compositions. The instrument has the additional capability of measuring the transmittance of liquid samples. Adaption for transmittance type spectrophotometric measurements can be made by simply directing the light path through a cuvette containing liquid sample.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
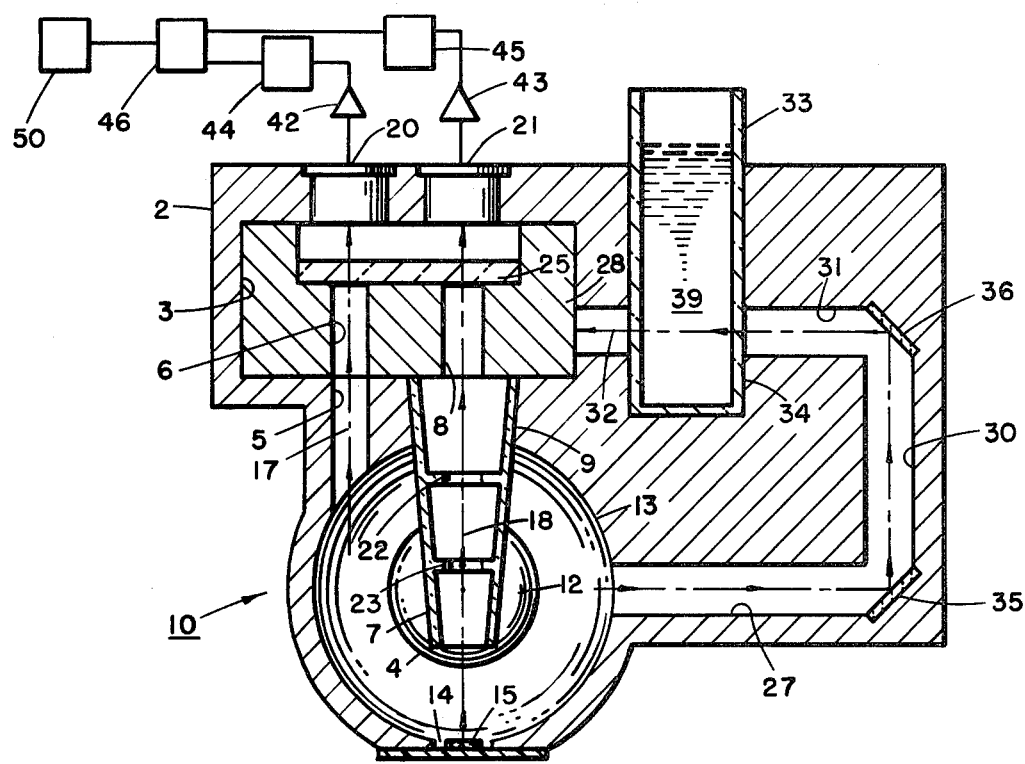
FIG. 1 is a partial cross-sectional side view of apparatus in accordance with the present invention which is useful for making reflectance measurements.
Figure 2:
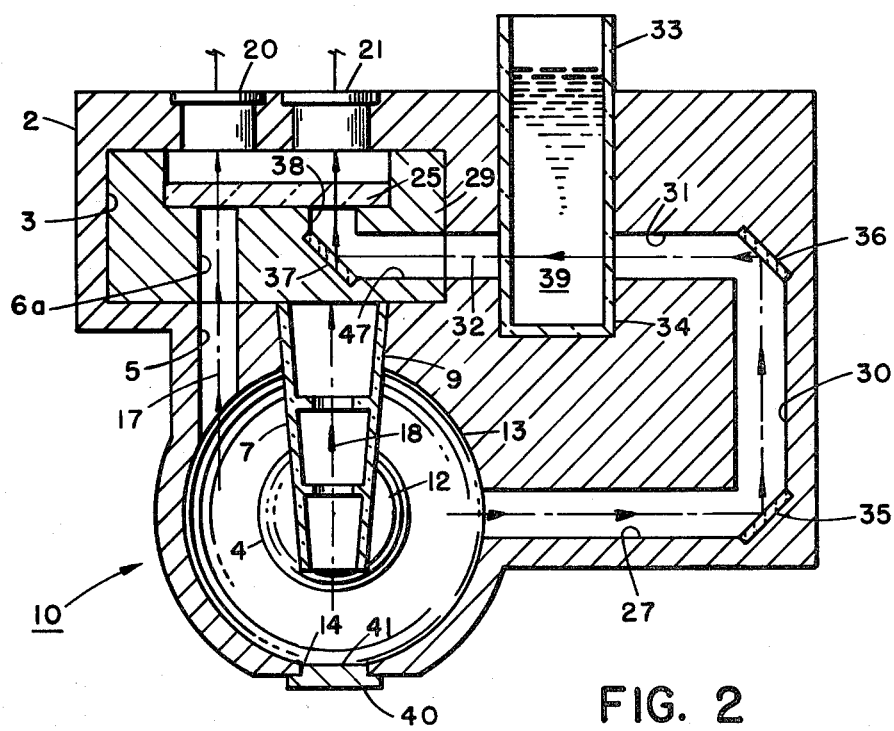
FIG. 2 is a partial cross-sectional side view of apparatus in accordance with the present invention which is useful in making transmittance measurements.

Referring now to the drawings, a spectrophotometer in accordance with the present invention is illustrated in FIGS. 1 and 2. Generally, the spectrophotometer comprises a light source capable of producing an extremely bright sample illuminating light of short duration; an integrating sphere; a light filter selected for transmission of a particular wavelength; separate light sensing means; and separate means defining light transmission paths for the passage of light from the integrating sphere to each light sensing means. A replaceable or repositionable module is also contemplated which is capable of changing the mode of operation for either reflectance or transmittance measurements.

More specifically, spectrophotometer 10 comprises light diffusing chamber or light integrating sphere 13 capable of uniformly distributing light and with compartment 3 for accomodation of module 28 in which filter 25 is mounted. A light source 12 is located near the rear of integrating sphere 13, casing 2 being formed thereat with opening 4 for passage of light from said light source into sphere 13.

Light source 12 is supplied with electrical energy through suitable electrical circuitry (not shown) and must be capable of producing an extremely bright light for a short period of time. Light source 12 produces white light having correlated color temperatures or spectral characteristics typical of a black body operating at 20,000° Kelvin and must produce a light intensity of at least 5,000° Kelvin. The duration of the light from source 12 is preferably between about one microsecond to about 100 microseconds, although it will be understood that the duration can for special applications be either shorter or longer. Light sources which are capable of meeting these requirements are of the bulb type, pulsed Xenon flashtubes. Model FX-108 B.U., manufactured by E.G.&G., Inc. of Salem, Mass., U.S.A., has been found to be particularly suitable for use as the light source in the present invention.

The purpose of integrating sphere 13 is to diffuse light from light source 12, and it will be understood that the location of light source 12 as shown in FIGS. 1 and 2 is only a preferred arrangement and that the light source could be located in other positions with respect to integrating sphere 13 and provide desired light diffusion. Preferably, however, the light source should not be in direct alignment with any light transmittance path from the integrating sphere.

The interior surface of integrating sphere 13 should be highly reflective. It has been found that an integrating sphere coated on the interior with magnesium oxide, barium sulfate, HALON resin (polytetrafluoroethylene) made by Allied Chemical Corporation of Morristown, N.J., U.S.A., or the like provides a satisfactory reflective surface. The size of the integrating sphere 13 is not critical. An integrating sphere as small as a ping-pong ball has been used successfully.

Casing 2 is also formed with means for positioning a sample at a sample position which means comprises opening 14 communicating with the interior of sphere 13 for exposure of sample 15 therein. Opening 14 must obviously be large enough to accomodate sample 15, which should extend only slightly into integrating sphere 13. In the embodiment illustrated by FIG. 1 spectrophotometer 10 is particularly adapted for making reflectance measurements of a sample which takes the form of a "dip-and-read" type reagent strip.

When spectrophotometer 10 is employed to determine the color reflectance from a test sample surface, such as the blood glucose test device of U.S. Pat. No. 3,298,789, the test device, which may take the form of a relatively thin strip, is placed across opening 14 with test sample surface 15 facing upward as viewed in FIG. 1. The test device of U.S. Pat. No. 3,298,789, for example, produces various color values corresponding to different levels of glucose in blood and these can be measured quite precisely by using the apparatus of the present invention.

Casing 2 and module 28 are formed with passage means defining separate light transmission paths or channels 17 and 18 which extend from integrating sphere 13 for the passage of light to separate light sensing means, such as photodetection means 20 and 21 mounted in casing 2 and exposed within compartment 3 as shown. Light transmission path 17 preferably extends generally tangentially from one side of integrating sphere 13 and is used to transmit light to reference photodetection means 20. Light transmission path 18, on the other hand, preferably extends from sample 15 diamentrically through sphere 13 in order to transmit light reflected from sample 15 directly to photodetection means 21.

Identical solid state silicon photodiodes, such as Model UVIOOB made by E.G.&G., Inc., of Salem, Mass., U.S.A., and Model S 876-33 BQ made by Hematsu Corporation, Middlesex, N.J., U.S.A., are preferred for use as the photodetection meeans 20 and 21 in accordance with the present invention.

Light transmission paths 17 and 18 should be adequate in size and of such a configuration to transmit essentially collimated light to the light sensing means. Path 17 is defined by coaxial generally cylindrical passages 5 and 6 in casing 2 and module 28, respectively, whereas path 18 is defined by frustoconicaltubular member 7 and coaxial cylindrical passage 8 formed in module 28 as shown. Member 7 is supported within frustoconical bore 9 coaxial with passage 8 and communicating between compartment 3 and sphere 13. Member 7 is preferably formed with spaced inwardly directed annular flanges or light baffles 22 and 23 defining coaxial circular openings which are of substantially the same diameter as the opening of the lower end of member 7 and which aid in collinating light passing therethrough.

While tubular members 7 is shown as having a frustoconical configuration, it will be understood that other configurations can be utilized. The surfaces of passages 5, 6, and 8 and the inner surfaces of member 7 are preferably painted or coated with a dull black finish to absorb any scattered or non collinated light rays. The casing 2, module 28 and member 7 can be made of any suitable material, such as metal or plastic. For example, member 7 can be made of molded white plastic or metal with an interior coated or painted dull black.

Before reaching photodetection means 20 and 21 light passing along paths 17 and 18 passes through an interference filter, such as filter 25, which is selected for transmission of a selected wavelength. In connection with the measurement of "dip-and-read" type reagent devices, filters which permit reflection of light having a wavelength of from about 300 nm to about 725 nm will normally be used. When transmittance measurements are made as hereinafter described, filters permitting the transmission of light having a wavelength of from about 250 nm to about 800 nm will normally be employed.

Filter 25 can be made of any suitable material such as glass, plastic or the like. Instead of one filter extending across both light transmission paths separate filters could, if desired, be employed.

The filters can be adapted in cartridge format to permit them to be readily inserted and withdrawn from the apparatus depending on the material or sample being analyzed. A multiple filter wheel (not shown) can also be used which is insertable into the apparatus and rotated as required to position the desired filter in light transmission paths 17 and 18.

By comparing the signals obtained from photodetection means 20 and 21, either visually from meters (see FIG. 3) or by using conventional, state of the art circuitry, illustrated diagrammatically in FIG. 1, the level of light reflected from sample 15 can be accurately determined at the wavelength selected by the filter. By comparing this value with one obtained from a reflectance standard the percent reflectance of the sample can be obtained. Means 20 is used to measure absolute light intensity in the spectrophotometer.

For some applications it is desirable to adapt the equipment such that light reaching reference photodetection means 20 is not filtered, i.e., no filter intersects path 17. This permits photodetection means 20 to measure substantially the total light available to the sample being measured. By selecting an appropriate filter to be placed across path 18 and then measuring the amount of light emitted by the sample, it is possible to ratio the outputs of the two photodetection means to produce the desired result.

The short time duration of the light pulse emitted from source 12 requires that peak values be determined and retained for a period sufficient to make the required measurement. One suitable way of processing the output of the photodetection means is to amplify the signals obtained by suitable amplifiers 42 and 43 and use the amplified signals to drive a pair of peak detector and hold circuits 44 and 45. The signals thus generated can be combined in a divider circuit 46 to make a ratio measurement and supply the result to suitable readout means 50 using any of several well known techniques. For example, a resistive voltage divider network (commonly referred to as a binary ladder network) can be driven with the reference signal peak detector output connected to the reference input of the ladder network. The ladder network is then successively adjusted until the output voltage of the ladder is equal to the sample signal voltage. Logic circuitry is used to control the successive approximation of the ladder network. The state of the ladder network at this point determines the attenuation made to make the reference signal equal to the sample signal. The resulting digital ratio value can then be suitably displayed or recorded on readout means 50.

The illustrated spectrophotometer 10 is adaptable to make transmittance measurements as well as reflectance measurements (see FIG. 2). To this end, the body or casing 2 is formed with connected cylindrical passages 27, 30, and 31, passage 27 opening radially into sphere 13, and passage 31 opening into compartment 3 through a sidewall surface thereof. Mirrors 35 and 36 are suitably mounted at the intersections of passage 27 and passage 30 and passage 30 and passage 31 as shown, said mirrors and passages defining a generally U-shaped portion of light transmitting path 32. As shown, passage 31 is intersected by a recess or well 34 in which a cuvette 33 is positioned to provide means for positioning a sample at a second sample position.

When instrument 10 is to be used for transmittance measurement, module 28 of FIG. 1 is replaced by module 29 shown in FIG. 2. Module 29 has a cylindrical passage 6a coaxially communicating with passage 5. However, in place of the passage 8 of module 28, module 29 is provided with connected right-angled cylindrical passages 38 and 47 and a mirror 37 suitably mounted at the juncture thereof, to direct light transmitted along path 32 toward photodetection means 21. It will be observed that when module 29 is used the flow of light from sphere 13 to detection means 21 along path 18 is blocked.

Mirrors 35, 36 and 37 are preferably first surface reflection mirrors, i.e., mirrors of the type which have aluminum coated outer surfaces, in order to provide maximum transmission of light along path 32. Passages 47, 38, 31, 30 and 27 are preferably painted or coated a dull black in order to minimize passage of extraneous noncollimated light along path 32.

Cuvette 33 can be made of any suitable material such as glass, quartz or plastic, e.g., acrylic, which will minimize interference with light passing along light transmission path 32. Cuvette 33 is adapted to accomodate sample 39 of a medium whose transmittance is to be measured. When spectrophotometer 10 is used for light transmittance measurement, sample opening 14 is closed by plug 40 suitably fixed therein. The inner end surface 41 of plug 40 preferably has high reflectance characteristics similar to those of the inner surface of integrating sphere 13.

In making transmittance measurements with spectrophotometer 10 as shown in FIG. 2, light from integrating sphere 13 passes to photodetection means 20 along path 17 and to photodetection means 21 along path 32. The light flowing along path 32 passes through cuvette 33 and sample 39 and the light reaching photodetection means 21 is compared with light reaching reference photodetection means 20. By comparing the ratio of output sensor means 20 and 21 with one obtained when cuvette 33 contains distilled water, the percentage of transmission is obtained.

It will be apparent to one skilled in the art that, if desired, a single dual-purpose module (not shown) can be used in place of both modules 28 and 29. Such dual-purpose module would be so constructed that when it is in one operative position within compartment 3, its cross-sectional configuration in the vertical plane of FIGS. 1 and 2 is the same as that of module 28 shown in FIG. 1, and when it is moved to another operative position within compartment 3, such as by rotation or otherwise, its cross-sectional configuration in the vertical plane of FIGS. 1 and 2 is the same as that of module 29 shown in FIG. 2. Thus, conversion of spectrophotometer 10 from reflectance measurement mode to transmittance measurement mode would require simply repositioning of the single dual-purpose module from one operative position to another, rather than replacement of the module 28 by module 29 as aforedescribed.

Figure 3:
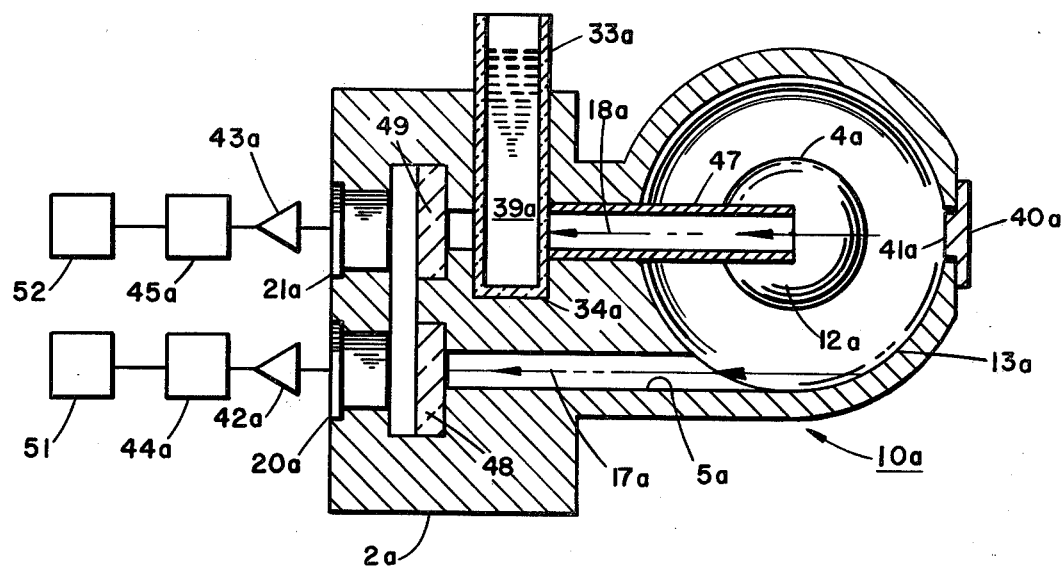
FIG. 3 is a partial cross-sectional side view of apparatus in accordance with another embodiment of the present invention which is useful for making either reflectance or transmittance measurements.

FIG. 3 illustrates a simplified embodiment of the invention capable of making either reflectance or transmittance measurements, depending upon the sample being measured. In FIG. 3 the parts corresponding to those in FIGS. 1 and 2 are indicated by the same reference numerals bearing the suffix a. Spectrophotometer 10a of FIG. 3 is similar to spectrophotometer 10 of FIGS. 1 and 2 except that light passes through the same transmission paths 17a and 18a for both reflectance and transmittance measurements. FIG. 3 illustrates a transmittance measurement being made with respect to sample 39a in cuvette 33a which is positioned in recess or well 34a which intersects path 18a. In order to make reflectance measurements, cuvette 33a is removed from well 34a and a sample (not shown) substituted for plug 40a. Thus, the embodiment illustrated in FIG. 3 eliminates the necessity for having to replace modules, reduces manufacturing expenses and provides for good light collimation passing to the light sensing means, i.e., photodetection means 20a and 21a.

As mentioned above, the signals of photodetection means 20a and 21a can be read visually from meters such as meters 51 and 52, respectively, supplied with output signals through amplifiers 42a and 43a and peak detector and hold circuits 44a and 45a.

It will be noted that in FIG. 3 light transmission path 18a passes through a cylindrical tube 47, rather than a frustoconically shaped tube such as tube 7 in FIG. 1. Also instead of single filter 25 used in FIG. 1, individual filters 48 and 49 which intersect paths 17a and 18a, respectively, are present in FIG. 3.

Figure 4:
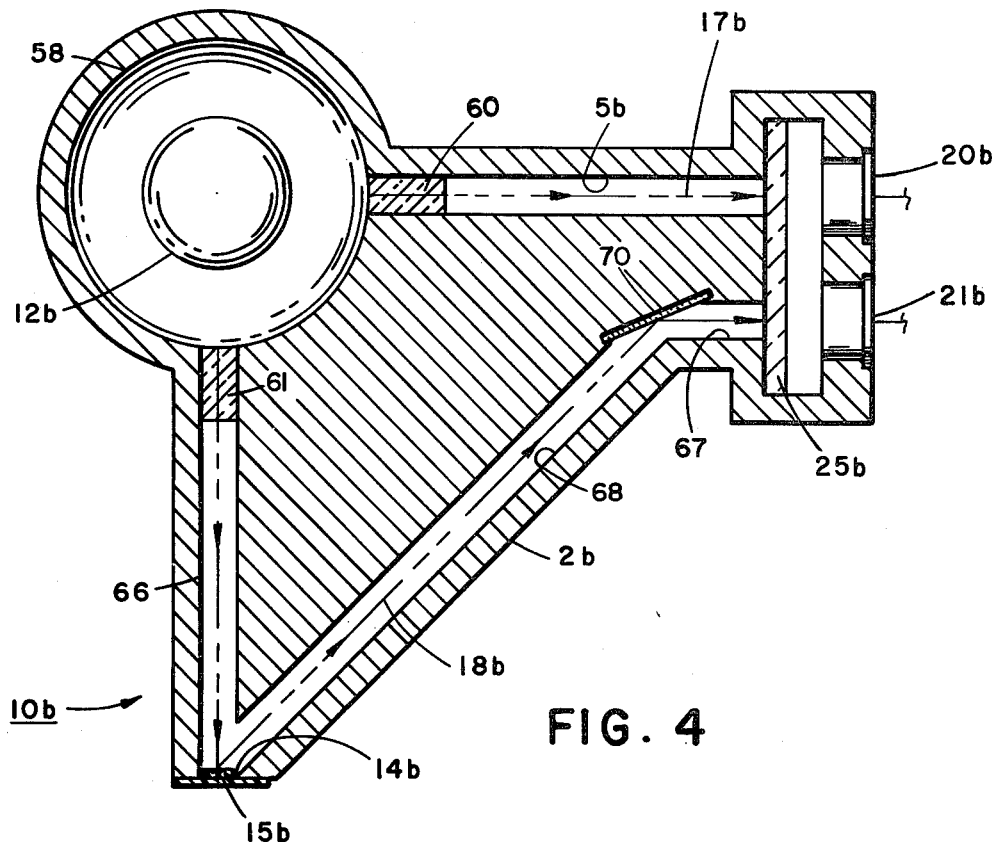
FIG. 4 is a partial cross-sectional side view of an alternative embodiment of the present invention.

An alternative and less preferred embodiment of the invention is illustrated in FIG. 4 wherein parts corresponding to those in FIGS. 1 and 2 are indicated by the same numerals bearing the suffix b. Casing 2b of instrument 10b is formed with a substantially spherical reflective light source housing or chamber 58 and with cylindrical passages 5b and 66 extending radially therefrom. Passage 66 terminates in sample opening 14b, and cylindrical passage 68 extends from said opening to passage 67 which is generally parallel with passage 5b, there being a first surface mirror 70 mounted at the juncture of passages 68 and 67, as shown. Light source 12b is located within chamber 58 so that said chamber does not primarily serve the light diffusing function served by integrating spheres 13 and 13a in FIGS. 1 to 3. In FIG. 4 light diffusion is accomplished by diffusing members 60 and 61 mounted in passages 5b and 66, respectively, adjacent the chamber 58. Members 60 and 61 may be made of frosted glass, cellulose acetate or the like and function to diffuse light from source 12b as it enters passages 5b and 66. The dull black finish within passages 5b, 66, 68 and 67 absorbs scattered light flowing into such passages from diffusing members 60 and 61. As with the structures of FIGS. 1 to 3, diffusion of light from the source and absorption of the scattered light within the light transmission passages reduces the intensity of the light from the source directed through said passages by limiting such light substantially to collimated rays directed axially of said passages.

In operation of spectrophotometer 10b of FIG. 4 sample test strip 15b is placed over opening 14b so that light from source 12b impinges on the sample after passing through diffusing member 61. Light reflected from the sample passes along path 18b through passages 68 and 67 and through filter 25b, and is sensed by photodetection means 21b. Light from source 12b also passes through diffusing member 60 and along path 17b through filter 25b to photodetection means 20b. The reflectance of the sample is arrived at by comparison of the light sensed by detector 21b with that sensed by detector 20b, in the same manner as in the other forms of the invention.

Figure 5:
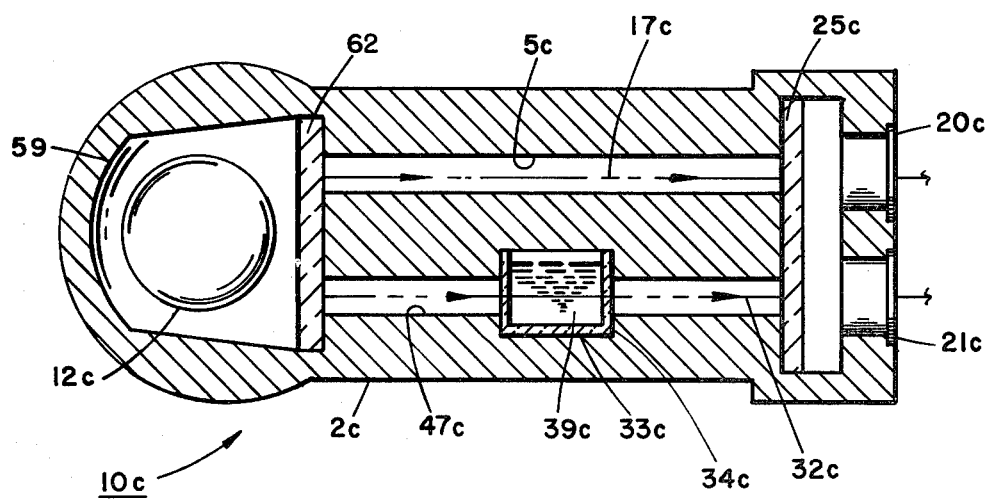
FIG. 5 is a partial cross-sectional side view of another alternative embodiment of the present invention.

Another alternative and less preferred embodiment of the invention is illustrated in FIG. 5 wherein parts corresponding to those in FIGS. 1 and 2 are indicated by the same numerals bearing the suffix c. Casing 2c of spectrophotometer 10c shown in FIG. 5 is formed with a parabolic reflective light source housing or chamber 59 accommodating light source 12c therein. Parallel cylindrical passages 5c and 47c are generally parallel with the direction of light rays from source 12c reflected from the parabolic inner surface of chamber 59 and are coaxially aligned with photodetection means 20c and 21c respectively. Passages 5c and 47c are adapted to receive light from source 12c through a single diffusing member 62. Passage 47c intersected by a cuvette or sample cell 33c accomodated within an appropriate opening 34c in housing 2c. Cuvette 33c is adapted to contain sample medium 39c, the transmittance of which is to be measured.

In operation of the form of the invention shown in FIG. 5, light emitted from source 12c enters passages 5c and 47c after passing through diffusing member 62 and travels along the light ransmission paths 17c and 32c toward light detection means 20c and 21c, respectively, the light flowing along path 32c passing through sample 39c. the transmittance of sample 39c is then arrived at by comparison of the light sensed by photodetection means 21c with that sensed by photodetection means 20c as in the other forms of the invention. As in the form of the invention shown in FIG. 4, diffusing member 62 in combination with the full black finish within passages 5c and 47c reduce the intensity of light from source 12c passing through said passages by limiting such light substantially to collimated light rays directed coaxially of said passages.

From the foregoing, it will be seen that this invention is adapted to attain all of the ends and objects hereinabove set forth, together with other advantages which are obvious and inherent. The preferred forms of the spectrophotometer disclosed herein can be used for making either reflectance or transmittance measurements. The spectrophotometer is light in weight and compact in size. Moreover, the accuracy of the spectrophotometer is extremely good and it can be operated by relatively unskilled personnel because of the unique combination of a flash tube type light source for producing a short burst of extremely bright light which is dispersed by the reflecting walls of an integrating sphere or of a light source housing. Utilization of the flash not only results in essentially eliminating heat problems, but it also materially reduces power requirements.

As previously noted, with conventional continuously operating light sources the amount of energy which can be dissipated is limited by physical factors. Moreover, electrodes evaporate rapidly, thus shortening lamp life.

In contrast, the present invention utilizes high levels of excitation while maintaining a low mean rate of energy dissipation in the lamp source. In addition, minimal exposure of photosensitive samples is accomplished. The light source utilized also eliminates concern about ambient light conditions. The spectrophotometer can thus be made as a convenient, lightweight, portable, relatively inexpensive unit.

Another advantage is the fact that the light sensing means used in the present case are solid state silicon photodiodes which, unlike photomultiplier tubes used in the past, significantly decrease the drift, noise or nonlinear operation.

The apparatus of the present invention is especially useful in the reflectance measurement of dip-and-read type reagent strips for determining the presence in urine samples of various components, such as glucose, occult blood, ketones, protein, and bilirubin.

Obviously, many modifications and variations of the invention as hereinbefore set forth can be made without departing from the spirit and scope thereof and therefore only such limitations should be imposed as are indicated by the appended claims.

What is claimed is:
1. Spectrophotometer apparatus comprising:
a light source capable of providing a bright light of short duration for illumination of a sample;
sample light sensing means;
reference light sensing means;
a light reflective integrating sphere interposed between said light source and said sample and between said light source and said reference sensing means;
means establishing a first light transmission path for the passage of light from said sample to said sample light sensing means, wherein said means establishing a first light transmission path has a reflectance mode in which it directs light reflected from a sample to a sample light sensing means and wherein said means establishing a first light transmission path also has an alternate transmittance mode in which it directs light passing through a sample to said sample light sensing means;

means defining a second light transmission path for the passage of light from said light source to the reference light sensing means;

filter means in at least one of said first and second light transmission paths, said filter means permitting the transmission of light having a wavelength between about 200 and about 1100 nanometers; and means for comparing the light received by the sample light sensing means with the light received by the reference light sensing means.

2. The apparatus of claim 1 in which the means defining said first and second light transmission paths are provided with means limiting light flow therethrough substantially to collimated rays.

3. The apparatus of claim 1 in which said light source is capable of producing a light intensity of at least 5,000° Kelvin for a duration of from about one microsecond to about 100 microseconds.

4. The apparatus of claim 1 wherein said sample and said reference light sensing means are solid state silicon photodiodes.

5. The apparatus of claim 1 wherein said first light transmission path is positioned to direct light reflected from said sample toward said sample light sensing means.

6. The apparatus of claim 1 wherein said first light transmission path is positioned to direct light which has passed through said sample toward said sample light sensing means.

7. The apparatus of claim 1 which further comprises a transparent receptacle for accomodation of a liquid sample, and wherein said first light transmission path is positioned to direct light transmitted through said sample toward said sample light sensing means.

8. The apparatus of claim 1 in which a sample is exposed within said integrating sphere such that light reflected from said sample is transmitted along said first light transmission path.

9. The apparatus of claim 1 wherein said filter means permits transmission therethrough of light having a wavelength of between about 300 and about 725 nanometers.

10. The apparatus of claim 1 wherein said filter means permits transmission therethrough of light having a wavelength of between about 250 and about 800 nanometers.

* * * * *